United States Patent [19]
Blake-Haskins et al.

[11] Patent Number: 5,788,951
[45] Date of Patent: Aug. 4, 1998

[54] DUAL COMPONENT DENTIFRICE COMPOSITION FOR FLUORIDATING TEETH CONTAINING COMPATIBLE SILICA ABRASIVE

[75] Inventors: John C. Blake-Haskins, Piscataway; Mary L. Colligan, Somerville; Michael A. Collins, Hazlet; Benjamin Y. Mandanas, Freehold; Abdul Gaffar, Princeton, all of N.J.

[73] Assignee: Colgate-Palmolive Company, New York, N.Y.

[21] Appl. No.: 826,846

[22] Filed: Apr. 8, 1997

[51] Int. Cl.$^6$ .............................. A61K 7/16; A61K 7/18
[52] U.S. Cl. .............................. 424/52; 424/49
[58] Field of Search .............................. 424/49–58

[56] References Cited

U.S. PATENT DOCUMENTS

| | | | |
|---|---|---|---|
| 4,353,890 | 10/1982 | Scott | 424/49 |
| 4,457,908 | 7/1984 | Scott | 424/49 |
| 4,562,066 | 12/1985 | Hayes et al. | 424/52 |
| 4,814,160 | 3/1989 | Carter et al. | 424/49 |
| 4,855,128 | 8/1989 | Lynch et al. | 424/49 |
| 5,236,696 | 8/1993 | Cattiis et al. | 424/49 |
| 5,571,502 | 11/1996 | Winston et al. | 424/62 |
| 5,603,922 | 2/1997 | Winston et al. | 424/49 |
| 5,605,675 | 2/1997 | Vsen et al. | 424/49 |
| 5,614,175 | 3/1997 | Winston et al. | 424/52 |

*Primary Examiner*—Shep K. Rose
*Attorney, Agent, or Firm*—Henry S. Goldfine; Paul Shapiro

[57] ABSTRACT

A composition and method is disclosed for fluoridating teeth using a two component dentifrice system in which the first component is stable, semi-solid, extrudable dentifrice composition containing a fluoride ion releasable hydrolyzable complex fluoride compound such as sodium fluorosilicate, in an aqueous vehicle in which a carrageenan gum having major kappa and lambda forms as the primary thickening agent and the abrasive is a silica providing an acid pH when slurried with water, and the second component is a semi-solid, extrudable dentifrice composition containing a calcium ion releasable compound and the abrasive and carrageenan gum in an aqueous vehicle. The first and second dentifrice compounds are maintained separate from the other until mixed for application to teeth.

14 Claims, No Drawings

DUAL COMPONENT DENTIFRICE COMPOSITION FOR FLUORIDATING TEETH CONTAINING COMPATIBLE SILICA ABRASIVE

BACKGROUND OF THE INVENTION

1. Field of the Invention

This invention is directed to a dentifrice composition containing fluoride compounds effective as anticaries agents and more particularly to a dual component dentifrice composition for fluoridating teeth.

2. The Prior Art

It has long been known to include fluoride containing compounds in dentifrices as anticaries agents, and it has been established that these compounds are effective to reduce the incidence of dental caries. Fluoride compounds which are deemed to be the most effective are sodium fluoride, sodium monoflurophosphate and stannous fluoride. The fluoride compounds are effective mainly due to the fluoride ions which improve the acid resistance of tooth enamel and accelerate recalcification of decayed teeth in their early stage when the decalcification has proceeded only slightly. The effect of improving the acid resistance of the enamel is believed to be due to the fact that the fluoride ions are incorporated into a crystal lattice of hydroxyapatite which is the main constituent of tooth enamel or, in other words, fluoride ions partially fluoridate hydroxyapatite and simultaneously repair the lattice irregularities.

The effectiveness of fluoride treatment in providing acid resistance is dependent upon the amount of fluoride ion which is available for deposition on the enamel being treated. It is, therefore, desirable to formulate dentifrice compositions which provide maximum fluoride ion availability in brushing solutions formed using the dentifrice.

U.S. Pat. No. 5,145,668 discloses a method of fluoridating teeth wherein there is mixed in the mouth a first component solution comprising a soluble calcium salt such as calcium $CaCl_2$ contained in a non-reactive vehicle and a second component solution containing a hydrolyzable complex fluoride compound such as sodium fluorosilicate ($Na_2SiF_6$) contained in a non-reactive vehicle, the mixing of the components resulting in hydrolysis of the complex fluoride compound and precipitation of calcium ($CaF_2$) fluoride and its deposition on tooth surfaces.

The method disclosed in U.S. Pat. No. 5,145,668 when practiced using the components in diluted liquid form as a rinse is an effective means of fluoridating teeth. However, efforts to practice the method using semi-solid, extrudable formulations such as toothpastes and gels have been unable to provide the theoretical maximum soluble fluoride because of the tendency for the ionic fluoride to be inactivated as the levels of the vehicle ingredients are increased to that required in a semi-solid product such as toothpaste. Such inactivation renders the fluoride originally included in the toothpaste to be unavailable for interaction with calcium ion to form precipitated $CaF_2$ for fluoride uptake by tooth enamel.

Thus, there is a clear need to formulate a semi-solid dentifrice product utilizing a hydrolyzable complex fluoride compound wherein the ingredients used to prepare the dentifrice composition do not participate in the inactivation of fluoride ion present so that optimum uptake of fluoride is accomplished when the fluoride containing dentifrice composition is mixed with a calcium ion containing dentifrice and applied to the teeth.

SUMMARY OF THE INVENTION

In accordance with the present invention there is provided a composition and method for fluoridating teeth, wherein two separate semi-solid components which contain ingredients which are reactive when mixed together and applied to the teeth, the first component being a stable, aqueous, semi-solid dentifrice composition containing a fluoride ion releasable, hydrolyzable complex fluoride compound and the second component containing a water soluble calcium ion releasable compound reactive with the fluoride compound, the vehicle for each component containing a humectant, an amorphous acidic silica abrasive and a sufficient amount of a carrageenan gum comprised of major portions of kappa and lambda constituents to impart an extrudible consistency to the components whereby maximum fluoride ion availability is provided, as precipitated calcium fluoride, upon mixing of the components and application to teeth.

Dentifrice components containing the fluoride ion releasable hydrolyzable complex fluoride or calcium ion releasable compounds in a vehicle prepared in accordance with the present invention are storage stable and exhibit the desirable rheological characteristics of a semi-solid toothpaste or gel, such characteristics including extrudability, proper viscosity flow rate and ribbon shape retention.

The semi-solid components of the dentifrice composition of the present invention are segregated prior to the point of use and when combined in a ribbon form on the bristles of a toothbrush, remain in a stand-up position on the toothbrush without substantially sinking through the bristles; the combined components complementing one another to provide a convenient and useful source of fluoride compound for increased effective inhibition of caries.

DESCRIPTION OF THE PREFERRED EMBODIMENTS

The first component of the dentifrice composition of the present invention contains a hydrolyzable complex fluoride salt as the source of fluoride. Hydrolyzable complex fluoride salts suitable for use in the practice of the present invention include alkali metal fluorosilicate, fluorostannate, fluorozirconate, fluoroborate and fluorophosphate salts such as sodium fluorostannate, sodium fluorosilicate, potassium fluorozirconate and potassium fluoroborate. The preferred fluoride compound for purposes of this invention is sodium hexafluorosilicate ($Na_2SiF_6$).

The hydrolyzable complex fluoride compound is incorporated in the first dentifrice component of the present invention at a concentration of about 0.1 to about 1% by weight, and preferably at about 0.25 to about 0.5% by weight. At these preferred concentrations, about 250 about 3000 parts per million (ppm), fluoride ion will be available to teeth when the combined first and second components of the dentifrice composition are admixed and applied to the teeth.

The second component of the dentifrice composition of the present invention, which is maintained physically separated from the first component until mixing before use, contains a water soluble calcium salt as a source of calcium ion. Examples of suitable soluble calcium salts include calcium chloride, calcium acetate, calcium butylate, calcium citrate, calcium lactate, calcium salicylate, and all other non-toxic salts of calcium and inorganic or organic acids which can dissolve in an aqueous solution to the level required for interaction with the hydrolyzable fluoride compound.

The calcium ion releasable salt is incorporated in the second component of the dentifrice composition of the present invention at a concentration of about 0.2% to about 4% by weight and preferably at about 1.0 to about 2.0% by weight. At the preferred concentrations, about 500 ppm to about 6000 ppm calcium ion (depending upon calcium salt used) will be available to teeth when the combined first and second components of the dentifrice composition are admixed and applied to the teeth.

The soluble calcium ion containing dentifrice component of the two-component dentifrice system of the present invention may include a buffer to adjust the pH to a substantially neutral pH, e.g., 6.5 to 7.5. Examples of such buffers include acetate salts and succinate salts. It is preferred that the buffer is an acetate salt when the fluoride and calcium ion containing dentifrice components are mixed together for interaction of the fluoride and calcium ions. The buffer aids in promoting the hydrolysis of the fluoride salt to occur at a steady, high rate, thus providing a continuous high level of fluoride ions to interact with the calcium ions to deposit $CaF_2$ during the time the teeth are exposed to the mixed two-component system. The buffer compound is generally included in the calcium ion containing dentifrice component of the present inventoin at a concentration of about 0.5 to about 3.0% by weight and preferably about 0.75 to about 2.0% by weight.

The calcium ion releasable salt is contained in a vehicle formulated to have a composition similar to the vehicle of the first dentifrice component, so that two components will be of similar physical characteristics, which will permit them to be equally coextrudable and allow the creation of a desirably attractive striped appearance when the components are of different colors and are extruded together from a toothpaste or pump container.

The vehicle for the separate components of the dentifrice composition of the present invention is formulated, as further defined hereinunder, to form a semi-solid product of desired consistency which is extrudable from a collapsible tube or pump. In general, the liquids that form the vehicle will comprise water, in an amount ranging from about 10 to about 35% by weight and preferably about 10 to about 20% by weight and a humectant comprised of glycerin, sorbitol or a mixture of both in an amount greater than about 40% by weight and preferably about 50 to about 70% by weight.

It is essential to the practice of the present invention to use a specific form of carrageenan gum having major amounts of kappan and lambda constituents as the major or predominant thickening agent for the vehicle used in the formulation of the dentifrice components of the present invention. Minor amounts of other thickening agents may be tolerated, but it is preferred that the carrageenan gum be the sole thickening agent. Carrageenan is a high molecular weight linear polysaccharide derived from sea plants which makes up approximately 2-7% of the plant and is found between the cellulosic fibers and is composed of repeating glactose units, and 3,6 anhydrogalactose (3,6-AG), both sulfated and nonsulfated, joined by alternating a 1–3, β 1–4 glycosidic linkages.

A preferred carrageenan gum is available commercially from FMC Corporation under the Trademark Viscarin TP-206 which typically contains 62% lambda, 30% kappa and 8% iota forms.

It has been found necessary to use carrageenan gum as the primary thickening agent in combination with an acidic silica abrasive in dentifrice components in which hydrolyzable complex fluoride salts are present in order to provide a stable, semi-solid, extrudable dentifrice which exhibits minimal loss of fluoride activity during storage. As will be further demonstrated, unexpectedly, only carrageenan gums having major portions of kappa and lambda constituents provide a stable efficacious cosmetically acceptable dentifrice composition. Other known thickening agents commonly used as dentifrice thickening agents such as guar gum, carboxymethyl cellulose and polyoxyethylene-polyoxypropylene glycol block copolymers or even carrageenan gums in which the lambda and kappa forms do not predominate, for example, iota carrageenan have been found to be incompatible with hydrolyzable complex fluoride compounds causing undue loss of availability of active fluoride ion.

The use of about 0.5 to about 3% carrageenan gum having major lambda and kappa constituents in the preparation of the dentifrice components of the present invention is sufficient to form a semi-solid, extrudable, shape retaining product which can be squeezed from a tube or displaced from a pump onto a toothbrush and will not fall between the bristles of the brush but rather, will substantially maintain its shape thereon.

Generally, the inclusion of abrasives in dentifrice formulations is necessary for effective cleaning of teeth by brushing. It has been determined that by including an abrasive such as silica having an acid pH in the composition, minimal inactivation of fluoride ion occurs.

It is also critical to the practice of the present invention that the abrasive material incorporated in the dentifrice components be a silica abrasive that provides an acidic pH and preferably a pH of about 3 to about 5, most preferably about 3.5 to 4.5 when slurried with water in a 95:5 water/silica composition weight ratio. Hydrolyzable complex fluoride salts are stable only in acidic environments. Acetic acid may be employed to adjust the pH of the hydrolyzable complex fluoride containing dentifrice component to acidic levels.

The acidic silica abrasive is generally included in the dentifrice components at a concentration of about 15 to about 50% by weight and preferably at a concentration of about 20 to about 40% by weight. A preferred commercially available acidic silica abrasive is Sylodent 783 available from W. R. Grace & Company, Baltimore, Md. Sylodent 783 has a pH of 3.4–4.2 when measured as a 5% by weight slurry in water.

Surfactants such as alkyl glycosides, may be included in the composition of the dentifrice components of the present invention to aid in the prophylactic action and to improve detersive and foaming properties without diminution of fluoride activity.

Alkyl glycosides used in the practice of the present invention are typically prepared by reacting glucose or an oligosaccharide with a fatty alcohol containing 12–22 carbon atoms and more preferable with alcohols containing an alkyl group having 12 to 18 carbon atoms. Alkyl glycosides having an alkyl group of 12–16 carbon atoms are preferred in the practice of the present invention. Alkyl glycosides prepared using polyglycoside is incorporated. Polyglycosides containing $C_{12}$–$C_{16}$ alkyl glycosides are available commercially from Henkel, Inc. under the trademark "Glucopon". An especially preferred Glucopon alkyl glycoside useful in the practice of the present invention is a non-ionic alkyl polyglycoside sold under the trademark Glucopon 625 characterized by the formula:

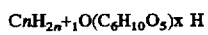

wherein n=12–16 and x (degree of polymerization)=1.5–1.6. The product has a pH of 11–12; a specific gravity of 25° C.

of 1.1 gms/ml; and a Brookfield viscosity at 35° C., 2 spindle, 5-10 RPM of about <4700 centistokes per second.

Surfactants such as the alkyl glycosides are incorporated in the oral care dentifrice component compositions of the present invention at a concentration of about 0.5 to about 3.0% by weight and preferably about 1.5 to about 2.5% by weight.

Various other materials may be incorporated into the dentifrice preparations of the present invention such as flavoring agents, sweetening agents and coloring materials such as dyes and pigments which are incorporated in the dentifrice compositions of the present invention in amounts which do not adversely affect the properties and characteristics desired in the dentifrice components.

Any suitable flavoring or sweetening materials may be employed in formulating a flavor for both the first and second components of the dentifrice compositions of the present invention. Examples of suitable flavoring constituents include flavoring oils, for example, oils of spearmint, peppermint, wintergreen, sassafras, clove, sage, as well as methyl salicylate. Suitable sweetening agents include lactose, maltose, sodium cyclamate and saccharine. Suitably, flavor and sweetening agents together comprise from about 0.01 to 5% or more of the composition. Preferably, the amount of flavoring oil is about 1.0 to about 2.5% by weight and the sweetening agent is from 0.1 to 4 or 0.1 to 0.5% by weight (the latter range being for artificial sweeteners, such as saccharine).

Coloring materials are generally commercially available food dyes and pigments which are inert with respect to the ingredients of the dentifrice components are included in the components at a concentration of about 0.05 to about 0.2% by weight.

The first dentifrice component of the present invention may be prepared by suitable mixing of the ingredients. For instance, in preparing the first component, the carrageenan gum is dispersed with humectants and water. The hydrolyzable complex fluoride compound, sweetener, silica abrasive, flavor and colorant are then separately added and uniformly dispersed. The dentifrice is then thoroughly deaerated (e.g., in vacuo) and packaged. The addition and mixing of the ingredients is conducted in a low humidity environment and preferably under a vacuum of 20-30 inches and preferably 28-30 inches mercury.

The second dentifrice component is prepared in a manner similar to that of the first component except that the calcium compound, pigment and buffer are substituted for the fluoride compound and buffering agent used in the preparation of the first dentifrice component.

The following specific Example illustrates the present invention. The individual dentifrice components described below were prepared by adding the carrageenan gum to a pre-mix of liquid (typically humectant and water) at a slightly elevated temperature (e.g., from 35° to 60° C.) with proportioning the ingredients to a creamy or gel consistency. Additional ingredients were then added. The amounts of the various ingredients are by weight unless otherwise indicated. The resultant dentifrice was then deaerated, flavor was introduced and the dentifrice was packed in tubes or other containers provided with means for physical separation of the individual dentifrice components.

EXAMPLE

A combined dentifrice composition of the present invention, designated "Composition X", composed of components A and B, was prepared using the following ingredients:

| Ingredients | Dentifrice Component A | Dentifrice Component B | % Total Ingredients when A & B Combined |
|---|---|---|---|
| Sodium Hexafluorosilicate (SHFS) | 0.370 | 0.000 | 0.185* |
| Calcium chloride dihydrate | 0.000 | 1.440 | 0.720 |
| Sylodent 783 | 35.000 | 35.000 | 35.000 |
| Glycerin | 25.000 | 25.000 | 25.000 |
| Sorbitol (70%) | 20.000 | 20.000 | 20.000 |
| Deionized Water | 15.970 | 12.155 | 14.063 |
| Glucopon 625 | 1.000 | 2.000 | 1.500 |
| Viscarin TP-206 | 1.100 | 1.100 | 1.100 |
| Flavor | 1.000 | 1.000 | 1.000 |
| Sodium acetate | 0.000 | 1.205 | 0.602 |
| Sodium Saccharin | 0.300 | 0.300 | 0.300 |
| Titanium dioxide | 0.000 | 0.500 | 0.250 |
| Sodium Hydroxide (50%) | 0.000 | 0.300 | 0.150 |
| Color solution | 0.200 | 0.000 | 0.100 |
| Acetic Acid | 0.060 | 0.000 | 0.030 |
| Total | 100.00% | 100.00% | 100.00% |

*contains 1100 ppm releasable F-

The fluoride delivery from components A and B when combined and mixed to form combined Composition X was assessed in vitro on hydroxyapatite (HAP) discs. This in vitro assessment is correlatable to in vivo delivery. Each circular 1.5×5 millimeter (mm) sintered HAP disc was mounted on a plastic stick with impression compound wax, so that only one 5 mm diameter face was exposed. The HAP discs were treated for 5 minutes with a slurry of 4 grams dentifrice in 12 ml deionized water in 15 ml plastic centrifuge tubes. The discs were then removed and rinsed for 15 seconds in deionized water. The discs were analyzed for fluoride uptake by etching in 1 ml 0.5M perchloric acid for 4 minutes in a shaker bath. The discs were removed, 1 ml NaOH-adjusted TISAB was added with sufficient NaOH to give a pH of 5.2 when combined with the $HClO_4$ etch solution. TISAB stands for total ionic strength adjusted buffer available from Orion Research, Cambridge, Mass. Fluoride in the etch solution was determined by direct potentiometry with an Orion fluoride ion electrode (Model No. 9409BN) wherein EMF is converted to ppm fluoride in the etchent by means of a logarithmic equation.

Two separate in vitro studies of the two component Composition X calcium/fluorosilicate dentifrice system were conducted. The fluoride uptake results for Composition X are recorded in Table I below.

For purposes of comparison, the procedure of the Example was repeated except combined dentifrice components designated Composition Y having substantially the same as composition as Composition X except no thickener was used and combined dentifrice components designated Composition Z which contained Viscarin TP-206 but no Sylodent 783.

A 1:3 dentifrice/water slurry of Compositions Y and Z were also assayed for fluoride uptake following the procedure of the Example. The fluoride uptake for comparative Compositions Y and Z are also recorded in Table 1.

In addition to fluoride uptake assays, fluoride bioavailability studies were conducted to determine whether the combined dentifrice components release sufficient fluoride during application to afford fluoride protection. Determinations of fluoride bioavailability from dentifrice Compositions X, Y and Z were performed by first preparing a slurry of the test composition followed by centrifugation to remove the solids in the dentifrice (such as abrasives and pigments), and then analysis of the supernatant solution by specific ion electrode to determine how much fluoride was released from the dentifrice. Analysis of fluoride bioavailability was conducted in the same manner as described above, with the exception that the analysis for fluoride was done by quantitative fluorine-19 ($^{19}F$) NMR rather than specific ion electrode as electrode method required that the samples be diluted which causes the fluorosilicate anion to hydrolyze. Quantitative $^{19}F$ NMR allows the measurement of soluble fluoride with minimal hydrolysis of the fluorosilicate anion. The analysis is performed by making a dilution of 1 part dentifrice to 3 parts buffer, followed by analysis of the supernatant by $^{19}F$ NMR at pH 3.5. The 1:3 dilution of dentifrice approximates the dilution of a dentifrice in the mouth by saliva during brushing. $^{19}F$ NMR is able to detect both fluoride ion and the fluorosilicate anion. In a typical experiment, the SHFS component formulated with hexfluorosilicate containing 2200 ppm F was found to produce 2165±30 ppm fluoride ion in the supernatant, with no fluorosilicate detected, yielding a recovery of 98.4%.

A commercially available dentifrice containing 1100 ppm fluoride as sodium fluoride which typically provides 95% fluoride bioavailability, designated Composition "W", was used as a control.

The results of the bioavailability of fluoride is also recorded in Table 1 below.

TABLE I

| Composition | Thickener Viscarin TP-206 (Wt %) | Abrasive Sylodent 783 (Wt %) | F-Uptake | % Available SHFS |
|---|---|---|---|---|
| X | 1.1 | 35 | 446 | 91.0 |
| Y | 0 | 35 | 72 | 0.02 |
| Z | 2 | 0 | 625 | 91.0 |
| W | — | — | 100 | — |

The results recorded in Table I shows that comparative Composition Z containing 2% Viscarin TP-206, but no silica abrasive provides 626% more fluoride uptake as the standard, commercially available 1100 ppm fluoride dentifrice Composition W, and a SHFS availability of 91%. However Composition Z would not have utility as a dentifrice for cleaning teeth due to the absence of an abrasive. Dentifrice Y containing 35% Sylodent 783 abrasive and no Viscarin TP-206, provided 28% less fluoride uptake than the standard fluoride dentifrice Composition W, and only 0.02% available SHFS. Composition X, a dentifrice prepared in accordance with the present invention which contained both 1.1% Viscarin TP-206 and 35% Sylodent 783, provided 446% as much fluoride uptake as the standard fluoride dentifrice Composition W and 91% available SHFS.

For purposes of further comparison, in a second series of tests, the procedure of the example was repeated except that in preparing dentifrice Compositions A and B, Viscarin TP-389 or carboxymethyl cellulose (CMC) was substituted for Viscarin TP-206 as the thickener or Zeodent 115 was substituted for Sylodent 783 as the silica abrasive.

Viscarin TP-389 is a carrageenan thickening gum, high in iota carrageenan content, containing approximately 96% iota, 4% lambda and no kappa carrageenan.

Zeodent 115 is a commonly used silica dentifrice abrasive, characterized by a neutral pH (pH of 5% slurry is 6.5–7.5).

The thickener and silica abrasive ingredients of the comparative dentifrice components are also listed in Table II below.

TABLE II

Thickener and Abrasive Present in Dentifrice Compositions

| Composition | Thickener (% by weight) | | Abrasive (% by weight) | | |
|---|---|---|---|---|---|
| | Viscarin TP 206 | CMC | Viscarin TP-389 | Sylodent 783 | Zeodent 115 |
| C | 1.1 | — | — | 35 | — |
| D | — | — | 1.1 | 35 | — |
| E | — | 1.1 | — | 35 | 35 |
| F | 1.1 | — | — | — | — |

The results are recorded in Table III below.

TABLE III

| Composition | Gum | Abrasive | F-Uptake | % Available SHFS |
|---|---|---|---|---|
| C | 1.1% Viscarin TP-206 | Sylodent 783 | 447 | 91 |
| D | Viscarin TP-389 | Sylodent 783 | 187 | 81 |
| E | CMC | Sylodent 783 | 72 | 81 |
| F | Viscarin TP-206 | Zeodent 115 | 137 | 64 |

The results recorded in Table III show that when the carrageenan thickener which has major lambda and kappa constituents (Viscarin TP-206-Compositon C) is replaced by a carrageenan thickener which does not contain major lambda and kappa forms (Viscarin TP-389-Compositon D) the fluoride uptake and available SHFS are substantially reduced even though the silica abrasive is the same (Sylodent 783). Further when Viscarin TP-206 is replaced by CMC (Composition F) the fluoride activity and available SHFS is further reduced.

When Zeodent 115 silica abrasive is substituted for Sylodent 783 (Example F), fluoride activity and available SHFS are also reduced.

What is claimed is:

1. A method for fluoridating teeth utilizing a semi-solid, extrudable, two component dentifrice system comprising the steps of (1) preparing as a first component a semi-solid, extrudable dentifrice composition containing a fluoride ion releasable hydrolyzable complex fluoride compound in an aqueous acidic vehicle in which the fluoride compound is stable, the vehicle containing a silica abrasive which exhibits an acid pH when measured as an aqueous slurry and as the primary thickening agent a carrageenan gum containing major portions of kappa and lambda forms and (2) preparing as a second component, a semi-solid, extrudable aqueous dentifrice composition containing a calcium ion releasable compound and the silica abrasive in an aqueous vehicle containing the carrageenan gum as the major thickening agent (3) maintaining the first and second dentifrice compounds separate from the other until application to teeth requiring fluoridation and (4) mixing the first and second components together to deposit calcium fluoride therefrom on contact with a tooth surface.

2. The method of claim 1 wherein the hydrolyzable complex fluoride compound is sodium fluorosilicate.

3. The method of claim 1 wherein the calcium compound is calcium chloride.

4. The method of claim 1 wherein the first component contains from about 0.1 to about 10.1% by weight fluoride ion.

5. The method of claim 1 wherein the second component contains from about 0.2 to about 4% by weight calcium ion.

6. The method of claim 1 wherein the silica abrasive exhibits a pH of 3.5–4.5 in an aqueous slurry of the abrasive.

7. The method of claim 1 wherein the carrageenan gum contains major kappa and lambda constituents.

8. A composition for fluoridating teeth comprising a semi-solid, extrudable, two component dentifrice system comprising (1) a first semi-solid aqueous, extrudable component containing a stable fluoride ion releasable hydrolyzable complex fluoride compound in an aqueous acidic vehicle containing a silica abrasive which exhibits an acid pH when measured in an aqueous slurry and as the primary thickening agent carrageenan gum containing major portions of kappa and lambda forms and (2) a second component comprising of a semi-solid, extrudable aqueous component containing a calcium ion releasable compound and the silica abrasive in an aqueous vehicle containing the carrageenan gum as the major thickening agent.

9. The composition of claim 8 wherein the hydrolyzable complex fluoride compound is sodium hexafluorosilicate.

10. The composition of claim 8 wherein the calcium compound is calcium chloride.

11. The composition of claim 8 wherein the first component contains from about 0.1 to about 1% by weight fluoride ion.

12. The composition of claim 8 wherein the second component contains from about 0.2 to about 4% by weight calcium ion.

13. The composition of claim 8 wherein the silica abrasive exhibits a pH of 3.5–4.5 in an aqueous slurry of the abrasive.

14. The composition of claim 8 wherein the carrageenan gum contains major kappa and lambda constituents.

* * * * *